United States Patent
Tann et al.

(10) Patent No.: US 8,883,685 B2
(45) Date of Patent: Nov. 11, 2014

(54) NITROGEN CONTAINING ISETHIONIC ACID SALT IN REGISTERABLE, STABLE AGRICULTURAL FORMULATIONS

(75) Inventors: R. Scott Tann, Sugar Land, TX (US); Howard M. Stridde, Shiner, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 0 days.

(21) Appl. No.: 13/264,470

(22) PCT Filed: Apr. 23, 2010

(86) PCT No.: PCT/US2010/032147
§ 371 (c)(1),
(2), (4) Date: Oct. 14, 2011

(87) PCT Pub. No.: WO2010/124152
PCT Pub. Date: Oct. 28, 2010

(65) Prior Publication Data
US 2012/0028802 A1    Feb. 2, 2012

Related U.S. Application Data

(60) Provisional application No. 61/172,398, filed on Apr. 24, 2009.

(51) Int. Cl.
*A01N 57/20* (2006.01)
*A01P 13/00* (2006.01)
*A01P 5/00* (2006.01)
*A01P 9/00* (2006.01)
*A01P 11/00* (2006.01)
*A01P 15/00* (2006.01)

(52) U.S. Cl.
CPC ........................................ *A01N 57/20* (2013.01)
USPC ............................ 504/206; 504/127; 504/148

(58) Field of Classification Search
None
See application file for complete search history.

(56) References Cited

U.S. PATENT DOCUMENTS

| 3,408,174 A | 10/1968 | Lindner |
| 3,692,512 A | 9/1972 | Sachnik |
| 3,799,758 A | 3/1974 | Franz |
| 3,951,842 A | 4/1976 | Prince et al. |
| 4,571,309 A * | 2/1986 | Lege ............................. 560/127 |
| 5,352,822 A * | 10/1994 | Blade et al. .................. 562/492 |
| 5,523,432 A | 6/1996 | Raths et al. |
| 6,746,988 B2 * | 6/2004 | Hopkinson et al. ........... 504/127 |
| 2001/0019997 A1 | 9/2001 | Wright |
| 2004/0138064 A1 * | 7/2004 | Tann ............................. 504/206 |
| 2008/0300161 A1 | 12/2008 | Schultz |

FOREIGN PATENT DOCUMENTS

| EP | 0 088 180 | 9/1983 |
| WO | WO 2010/009820 A | 1/2010 |

OTHER PUBLICATIONS

Gillco Ingredients, "Food Emulsifiers", <http://www.gillco.com/pr_emulsifiers.php>, Sep. 26, 2008. p. 1.*
antiagingchoices.com, "Sodium Lauryl Sulfate (SLS) in your Personal Care Products", <http://antiagingchoices.com/harmful_ingredients/sodium_lauryl_sulfate.htm>, Copyright 1999-2009, Revised Feb. 13, 2012, p. 1.*
World Health Organization, "Glyphosate and AMPA in Drinking-water: Background document for development of WHO Guidelines for Drinking-water Quality", copyright World Health Organization 2005, pp. 9.*
Pesticide News, "Glyphosate Fact Sheet", <http://www.pan-uk.org/pestnews/Actives/glyphosa.htm>, No. 33, Sep. 1996, p. 1-4.*
Alanwood, "Compendium of Pesticide Common Names: Herbicides", <http://www.alanwood.net/pesticides/class_herbicides.html>, published May 26, 2006, p. 1-12.*
SIELC Applications, "HPLC Application of HPLC Separation of Glyphosate Production Intermediates", <http://www.sielc.com/Application-HPLC-Separation-of-Glyphosate-Production-Intermediates.html>, © 2002-2013, p. 1.*

* cited by examiner

*Primary Examiner* — Tracy Vivlemore
*Assistant Examiner* — Monica Shin
(74) *Attorney, Agent, or Firm* — Huntsman International LLC

(57) ABSTRACT

Embodiments of the present invention disclose an agricultural composition that is a registerable, stable agricultural formulation that includes at least one nitrogen containing isethionic acid salt, at least one plant protection product, at least one surfactant and optionally at least one inert ingredient.

17 Claims, No Drawings

NITROGEN CONTAINING ISETHIONIC ACID SALT IN REGISTERABLE, STABLE AGRICULTURAL FORMULATIONS

CROSS-REFERENCE TO RELATED APPLICATIONS

This application is the National Phase of International Application PCT/US2010/032147 filed Apr. 23, 2010 which designated the U.S. and which claims priority to U.S. Provisional App. Ser. No. 61/172,398 filed Apr. 24, 2009. The noted applications are incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates generally to agricultural compositions, in particular to registerable, stable agricultural formulations that include isethionic acid and/or salts thereof.

2. Background of the Invention

It is known that multivalent water hardness ions (calcium, magnesium, iron, etc.) can inhibit the efficacy of numerous pesticides, especially weak acid herbicides. For example, the efficacy of glyphosate (N-phosphonomethyl glycine) is compromised when combined in a hard water solution containing calcium and magnesium ions. Calcium and magnesium ions will bind to glyphosate and render it less effective. This phenomenon is typical with aminophosphate herbicides as well as other weak acid herbicides. To overcome this problem, current commercial manufacturers of weak acid herbicide formulations recommend on their label the inclusion of ammonium sulfate in the spray solution as a water conditioner. Numerous research studies have shown that ammonium sulfate in the spray tank solution will reduce the effect of the hard water ions on the efficacy of glyphosate formulations.

However, spray solutions that use ammonium sulfate have drawbacks Ammonium sulfate grades range in color and purity. Often the applicator is forced to handle many large non-dispersing lumps of ammonium sulfate which have absorbed moisture. These materials are hard to handle and do not dissolve easily in the spray solution. This leads to plugged filter screens in the spray rig and plugged nozzle tips during applications.

One way to overcome this disadvantage is to formulate the ammonium sulfate into the desired weak acid herbicide formulation. Formulations containing the amount of ammonium sulfate necessary to provide the benefit from ammonium sulfate often cannot be achieved due to solubility limits of the combination of ammonium sulfate and the desired weak acid herbicide. Furthermore the surfactants necessary for the wetting and or spreading of the herbicidal active ingredient are unavailable due to being made incompatible and insoluble in the formulation. The pesticide producer is therefore forced to choose between the hard water antagonism for the herbicide and the desired surface modification properties imparted by the surfactant.

BRIEF SUMMARY OF SOME OF THE PREFERRED EMBODIMENTS

In a first aspect, embodiments of the present invention disclose an agricultural composition that is a registerable, stable agricultural formulation that includes at least one nitrogen containing isethionic acid salt, at least one plant protection product, at least one surfactant, and optionally at least one inert ingredient.

In an embodiment of the present invention, the at least one nitrogen containing isethionic acid salt has a cationic nitrogen containing group that is an alkyl amine, an alkylalkanolamine or a cyclic amine.

In an embodiment of the present invention, the at least one nitrogen containing isethionic acid salt comprises an ammonium isethionic acid salt.

In an embodiment of the present invention, the nitrogen containing isethionic acid salt comprises a derivative of a nitrogen containing isethionic acid salt.

In an embodiment of the present invention, the derivative of a nitrogen containing isethionic acid salt comprises, nitrogen containing isethionic methyl acid salt.

In an embodiment of the present invention, the at least one nitrogen containing isethionic acid salt further comprises isethionic acid.

In an embodiment of the present invention, the plant protection product is selected from the group consisting of: an insecticide, a fungicide, a biocide, a molluscicide, an algaicide, a plant growth regulator, an anthelmintic, a rodenticide, a nematocide, an acaricide, an amoebicide, a protozoacide, a crop safener and a combination thereof.

In an embodiment of the present invention, the at least one surfactant comprises one or more surface active agents capable of reducing the surface tension of water.

In an embodiment of the present invention, the inert ingredient comprises one or more of the following is selected from the group consisting of: a solvent, a water, a glycol, including polyalkyleneglcols a glycol ether, an emetic, a dye, a fragrance, an alcohol co-solvent and a combination thereof, and other utility inert ingredients.

In a second aspect, embodiments of the present invention disclose a method of treatment of vegetation comprising the step of contacting the registerable, stable agricultural formulation to vegetation or soil.

In a third aspect, embodiments of the present invention disclose a method of treatment of a substrate comprising the step of contacting the registerable, stable agricultural formulation to the substrate requiring treatment.

The foregoing has outlined rather broadly the features of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other compositions for carrying out the same purposes of the present invention. It should also be realized by those skilled in the art that such equivalent compositions do not depart from the spirit and scope of the invention as set forth in the appended claims.

DETAILED DESCRIPTION OF THE PREFERRED EMBODIMENTS

In embodiments of the present invention, nitrogen containing isethionic acid salts may function as water conditioners at a lower level of dissolved solids than does ammonium sulfate, but also they surprisingly exhibit solubilities which allow for the formulation of other inert ingredients necessary to achieve a registerable agricultural formulation.

Embodiments of the present invention disclose an agricultural composition that includes at least one nitrogen containing isethionic acid salt, at least one plant protection product, at least one surfactant, and optionally at least one inert ingredient. The agricultural composition is a registerable, stable agricultural formulation.

Embodiments of the present invention include at least one nitrogen containing isethionic acid salt. The nitrogen containing species of the salt may be any cationic nitrogen containing group. Examples of cationic nitrogen containing groups may be alkyl amines, alkylalkanolamines and cyclic amines. Specific examples of cationic nitrogen containing groups may include ammonium, alkyl amines, fatty amines (e.g. tallow amine, coco amine and soya amines), and their alkoxylated derivatives, alkyldiamines and their alkoxylated derivatives, alkylpolyamines and their alkoxylated derivatives, ethyleneamines, ethanolamines, morpholines, substituted propylamines, polyol amines (e.g. JEFFAMINE® amines as available from the Huntsman Corporation of The Woodlands, Tex.) and combinations thereof. One skilled in the art will recognize appropriate nitrogen containing cationic species to use in embodiments of the present invention.

The anionic part of the salt includes isethionic acid. Isethionic acid has the general formula $HSO_3$—$CH_2$—$CH_2$—OH. Two versions of isethionic acid, the second being a derivative of the first (isethionic methyl acid), may be produced using the following reactions:

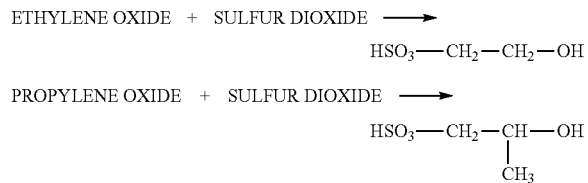

The isethionic acid is neutralized to form the salt. The isethionic acid may be neutralized, separately or in combination, with such reactants as ammonia and other nitrogen containing groups listed above and/or in a preferred embodiment tallow amine ethoxylates. For example, a tallow amine would form the following salt with isethionic acid.

TALLOW AMINE→R—N⁻(EO)$_{X\&Y}$ wherein x,y are from 2-30 and EO refers to ethylene oxide.

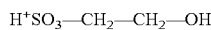

The nitrogen containing isethionic acid salt may further include isethionic acid (non-neutralized species). In another embodiment, the nitrogen containing isethionic acid salt comprises derivatives of nitrogen containing isethionic acid salts. An example of a derivative of a nitrogen containing isethionic acid salt would be nitrogen containing isethionic methyl acid salt (whose non-nuetralized acid is featured above). One skilled in the art, with the benefit of this disclosure, will recognize appropriate nitrogen containing isethionic acid salts for use in the present invention.

Embodiments of the present invention further include a plant protection product. The plant protection products may include water soluble herbicides, fertilizers and combinations thereof, including without limitation, aminophosphate herbicides. In an embodiment, the plant protection products may include without limitation, glyphosate, glufosinate, bipyridylquaternary ammonium salts (bipyridinium salt) such as paraquat and diquat, salts of phenoxy acids such as 2,4-dichlorophenoxyacetic acid, meta-chlorophenoxyacetic acid (MCPA), picloram, triclopyr and fluoroxypyr, and bromoxynil.

As used herein, "glyphosate" means N-phosphonomethylglycine in its acid form or any agriculturally acceptable salt thereof as well as any composition or formulation containing a glyphosate herbicide. "Glyphosate herbicide" means any form of glyphosate which in aqueous solution provides glyphosate anions along with suitable cations or glyphosate acid. Examples of such suitable cations are alkali metal cations, for instance sodium and potassium, and ammonium and substituted ammonium cations. The latter include cations derived from primary or secondary amines such as isopropylamine or dimethylamine, and from diamines such as ethylenediamine. Glyphosate herbicide includes the isopropylamine salts of glyphosate and other agriculturally acceptable salts of glyphosate such as those disclosed in U.S. Pat. No. 3,799,758. Further, examples of agriculturally acceptable salts of glyphosate are trimethyl-sulfonium salt ("sulfosate") or aminoguanidine salts as disclosed in EP-A-0 088 180. Because glyphosate has more than one replaceable hydrogen atom, mono- and di-salts are possible, as well as mixtures of such salts. Typical glyphosate salts are the potassium, ammonium and trimethylsulphonium salts as well as the mixed alkylsulfonium salts and trialkylammonium salts.

As used herein, "glufosinate" means N-phosphonomethylalanine in its acid form or any agriculturally acceptable salt of thereof.

In other embodiments, the plant protection product may include, without limitation: insecticides, fungicides, biocides, molluscicides, algaicides, plant growth regulators, anthelmintics, rodenticides, nematocides, acaricides, amoebicides, protozoacides, crop safeners and combinations thereof. Examples of such agricultural ingredients can be drawn from the Pesticide Dictionary (contained in the Farm Chemicals Handbook) or the British Crop Protection Society Pesticides Manual, the contents of which are incorporated herein by reference. Plant protection products further include chemical substances that are described as "biologically-active ingredients" in International Publication No. WO 2010/009820, which is hereby incorporated by reference. WO 2010/009820 includes, without limitation, descriptions and lists of various pesticides, fungicides, herbicides, insecticides, plant growth regulators, rodenticides, miticides, moluscicides, nematicides and antimicrobials which may be used in embodiments of the present invention. One skilled in the art, with the benefit of this disclosure, will recognize suitable plant protection products and combinations thereof for use in this invention.

Embodiments of the present invention further include at least one surfactant. The at least one surfactant may include one or more surface active agents capable of reducing the surface tension of water. Surfactants of the present invention may include, without limitation, phosphate esters of alkyl ethoxylates and/or alkylaryl ethoxylates; alkylamine ethoxylates and/or etheramine ethoxylates and their dimethylamino quaternary derivatives; alkyldiamine ethoxylates, alkylamine oxides, ethanolamines (such as monoethanolamine (MEA), diethanolamine (DEA), triethanolamine (TEA)) and combinations thereof. Surfactants generally include all surfactants which may show up in registerable, stable agricultural formulations. Such surfactants may include, without limitation: aldypolysaccharides, sorbitol and sorbitan esters and ethoxylates of such esters, fatty acid ethoxylates ethoxylated fatty alkanolamines, sulfosuccinates, naphthalene sulfonates, polyoxyethylene polyoxypropylene co-block polymers, alkyl polyoxyethylene polyoxypropylene copolymers, alkyl ethoxylates, aklyaryl ethoxylates, alcohol ether sulfates, alcohol sulfates, alpha olefin sulfonates, salts of dodecylbenzene sulfonic acid, and combinations thereof. One skilled in the art will recognize other suitable surfactants for use in embodiments of the present invention.

Embodiments of the present invention optionally include at least one inert ingredient. Inert ingredients may include, without limitation: solvents, glycol (including without limitation polyalkylene glycols such as ethylene glycol, propylene glycol, and diethylene glycol); glycol ethers; water; alcohol co-solvents; emetics, dyes, fragrances and combinations thereof. One skilled in the art will recognize other appropriate inert ingredients to include in embodiments of the present invention.

Agriculture compositions of the present invention are registerable, stable agricultural formulations. Registerable, stable agricultural formulations are usually agricultural products that will be further diluted. However in some cases ready to use registerable formulations may be used directly by homeowners and professional pest control agents in the treatment of household pests. These mixes must be stable for extended periods of time as dictated by government agencies so they have an acceptable shelf life. This type of agricultural formulation requires governmental registration: for example, in the United States, registration is required through Federal Insecticide, Fungicide and Rodenticide Act (FIFRA). Registerable, stable commercial formulations may be categorized as a soluble concentrate (SL), as defined under the classifications developed at the Food and Agriculture Organization of the United Nations/World Health Organization (FAO/WHO) Joint Meeting on Pesticide Specifications (Rome 2006). Registerable, stable commercial formulations are distinguishable from field ready sprays or tank mixes because they have an appreciably stable shelf life and need government (for example, FIFRA) registration numbers. Stable and registerable formulations must confirm to the standards recognized for such as recognized by the relevant government authority. Examples of such formulation stability standards include those set by CropLife International. Such standards are often set according to results of tests prescribed by the CIPAC and ASTM organizations. Field ready sprays or tank mixes are typically diluted, then mixed by a farmer and then applied. Field ready sprays or tank mixes do not, in most instances, have appreciable shelf life and in some countries such as the United States they do not require registration numbers.

Compositions disclosed herein may further comprise other utility additives. Additives may include humectants, antifreeze agents, antifoaming agents, dyes and non-surfactant adjuvants such as emetics and-buffering agents. One skilled in the art, with the benefit of this disclosure, will recognize other appropriate additives for use in embodiments of the present invention.

Embodiments of the present invention also disclose a method of treatment of vegetation comprising the step of contacting the agricultural compositions of the present invention to vegetation or soil. Compositions of the present invention may be applied to plants and soils.

Embodiments of the present invention also disclose a method of treatment of a substrate comprising the step of contacting the agricultural compositions of the present invention to the substrate. Such examples may include public health uses of pesticides or animal health formulations. As an example, insecticides may be applied to floors and walls as a preventative treatment. Also, fungicides may be applied to seeds and soils. Compositions of the present invention may be used in other appropriate applications.

The present invention will be further illustrated by a consideration of the following examples, which are intended to be exemplary of the invention.

EXAMPLES

Comparison Example 1

Two formulations were produced, one using ammonium sulfate (commercial control) and the other using ammonium isethionate (embodiment of the present invention). The formulations' compositions are shown in Table 1. The plant protection product is a commercially available isopropylamine salt of glyphosate. The surfactant is TERWET® 3780 surfactant blend. This surfactant is a formulated ethoxylated tallow amine blend that is commercially available from Huntsman Corporation of The Woodlands, Tex.

TABLE 1

| Ingredients | Example 1 weight % | Control 1 weight % |
|---|---|---|
| PLANT PROTECTION PRODUCT (IPA GLYPHOSATE (62%)) | 66.0 | 66.0 |
| SURFACTANT (TERWET ® 3780 SURFACTANT BLEND) | 7.5 | 7.5 |
| INERT INGREDIENT (WATER) | 16.5 | 16.5 |
| AMMONIUM ISETHIONATE | 10.0 | — |
| AMMONIUM SULFATE | — | 10.0 |
| | 100.0 | 100.0 |
| Results: | CLEAR | HEAVY CRYSTALS |

Comparison Example 1 shows that clear, homogeneous formulations can be made with ammonium isethionate that cannot be made with an equivalent amount of ammonium sulfate.

Although the present invention and its advantages have been described in detail, it should be understood that various changes, substitutions and alterations may be made herein without departing from the spirit and scope of the invention as defined by the appended claims.

What is claimed is:

1. An agricultural composition comprising:
    a) at least one nitrogen containing isethionic acid salt, wherein a nitrogen containing species of the salt is selected from the group consisting of alkylalkanolamines, cyclic amines, ammonium, fatty amines and their alkoxylated derivatives, alkyldiamines and their alkoxylated derivatives, alkylpolyamines and their alkoxylated derivatives, morpholines, polyol amines and combinations thereof,
    b) at least one plant protection product selected from the group consisting of a herbicide, a fertilizer, and combinations thereof,
    c) at least one surfactant, and
    d) optionally at least one inert ingredient,
    wherein the agricultural composition is a registerable, stable agricultural formulation.

2. A composition according to claim 1 wherein the at least one nitrogen containing isethionic acid salt has a cationic nitrogen containing group that is an alkylalkanolamine or a cyclic amine.

3. A composition according to claim 1 wherein the at least one nitrogen containing isethionic acid salt comprises an ammonium isethionic acid salt.

4. A composition according to claim 1 wherein the at least one nitrogen containing isethionic acid salt comprises a derivative of a nitrogen containing isethionic acid salt.

5. A composition according to claim 4 wherein the derivative of a nitrogen containing isethionic acid salt comprises nitrogen containing isethionic methyl acid salt.

6. A composition according to claim 1 wherein the at least one nitrogen containing isethionic acid salt further comprises isethionic acid.

7. A composition according to claim 1 wherein the at least one surfactant comprises one or more surface active agents capable of reducing the surface tension of water.

8. A composition according to claim 1 wherein the inert ingredient is selected from the group consisting of: a solvent, a water, a glycol, a glycol ether, an emetic, a dye, a fragrance, an alcohol co-solvent and a combination thereof.

9. A method of treatment of a substrate comprising the step of contacting the agricultural composition as described in claim 1 to the substrate.

10. The composition of claim 1, wherein the herbicide is water soluble.

11. The composition of claim 1, wherein the herbicide comprises glyphosate.

12. The composition of claim 1, wherein the herbicide is selected from the group consisting of glufosinate, bipyridlylquaternary ammonium salts (bipyridinium salt), paraquat, diquat, salts of phenoxy acids, 2,4-dichlorophenoxyacetic acid, meta-chlorophenoxyacetic acid (MCPA), picloram, triclopyr and fluoroxypyr, and bromoxynil.

13. The composition of claim 1, wherein the herbicide comprises an aminophosphate herbicide.

14. The composition of claim 1, wherein the herbicide comprises a weak acid herbicide.

15. An agricultural composition comprising:
  a) at least one nitrogen containing isethionic acid salt, wherein a nitrogen containing species of the salt is selected from the group consisting of alkylalkanolamines, cyclic amines, ammonium, fatty amines and their alkoxylated derivatives, alkyldiamines and their alkoxylated derivatives, alkylpolyamines and their alkoxylated derivatives, morpholines, polyol amines and combinations thereof,
  b) at least one plant protection product selected from the group consisting of a biocide, a molluscicide, an algaicide, a plant growth regulator, an anthelmintic, a rodenticide, a nematocide, an acaricide, an amoebicide, a protozoacide, a crop safener and combinations thereof,
  c) at least one surfactant, and
  d) optionally at least one inert ingredient,
  wherein the agricultural composition is a registerable, stable agricultural formulation.

16. A method of treatment of vegetation comprising:
forming an agricultural composition comprising:
  a) at least one nitrogen containing isethionic acid salt, wherein a nitrogen containing species of the salt is selected from the group consisting of alkylalkanolamines, cyclic amines, ammonium, fatty amines and their alkoxylated derivatives, alkyldiamines and their alkoxylated derivatives, alkylpolyamines and their alkoxylated derivatives, morpholines, polyol amines and combinations thereof,
  b) at least one herbicide, and
  c) at least one surfactant, wherein the agricultural composition is a registerable, stable agricultural formulation; and
contacting the agricultural composition with vegetation or soil.

17. The composition of claim 1, wherein the fatty amine is selected from the group consisting of tallow amine, coco amine, and soya amine.

* * * * *